US010973878B2

(12) United States Patent
Tian et al.

(10) Patent No.: US 10,973,878 B2
(45) Date of Patent: Apr. 13, 2021

(54) RECOMBINANT FUSION PROTEIN CONTAINING AN ANTI-PD-L1 ANTIBODY

(71) Applicant: ImmuneOnco Biopharmaceuticals (Shanghai) Co., Ltd., Shanghai (CN)

(72) Inventors: Wenzhi Tian, Shanghai (CN); Song Li, Shanghai (CN)

(73) Assignee: IMMUNEONCO BIOPHARMACEUTICALS (SHANGHAI) CO., LTD., Shanghai (CN)

( * ) Notice: Subject to any disclaimer, the term of this patent is extended or adjusted under 35 U.S.C. 154(b) by 39 days.

(21) Appl. No.: 16/170,024

(22) Filed: Oct. 24, 2018

(65) Prior Publication Data
US 2019/0125834 A1    May 2, 2019

Related U.S. Application Data

(60) Provisional application No. 62/577,704, filed on Oct. 26, 2017.

(51) Int. Cl.
| | | |
|---|---|---|
| *C12N 15/70* | (2006.01) | |
| *C12N 15/81* | (2006.01) | |
| *A61K 38/17* | (2006.01) | |
| *A61P 37/00* | (2006.01) | |
| *A61P 1/00* | (2006.01) | |
| *A61P 35/00* | (2006.01) | |
| *C07K 14/705* | (2006.01) | |

(52) U.S. Cl.
CPC ............ *A61K 38/1774* (2013.01); *A61P 1/00* (2018.01); *A61P 35/00* (2018.01); *A61P 37/00* (2018.01); *C07K 14/70596* (2013.01); *C12N 15/70* (2013.01); *C12N 15/81* (2013.01)

(58) Field of Classification Search
CPC .......... C07K 2319/70; C07K 14/70596; A61K 38/1774
USPC ............................... 424/133.1, 134.1, 178.1
See application file for complete search history.

(56) References Cited

U.S. PATENT DOCUMENTS

| | | | |
|---|---|---|---|
| 10,086,042 B2 * | 10/2018 | Schreiber ............... | A61P 35/00 |
| 10,183,060 B2 * | 1/2019 | Schreiber ............... | A61P 37/04 |
| 10,188,701 B2 * | 1/2019 | Schreiber ........... | A61K 38/1774 |
| 10,316,093 B2 * | 6/2019 | Cheung ................... | A61K 35/17 |
| 10,449,233 B2 * | 10/2019 | Schreiber ............... | C07K 14/00 |
| 10,493,128 B2 * | 12/2019 | Schreiber ............... | A61P 37/02 |
| 10,525,102 B2 * | 1/2020 | Schreiber ............... | A61P 35/00 |
| 10,543,253 B2 * | 1/2020 | Schreiber ............... | C07K 14/00 |
| 10,646,545 B2 * | 5/2020 | Schreiber ............. | A61K 38/177 |
| 10,653,748 B2 * | 5/2020 | Schreiber ............... | C07K 19/00 |
| 10,660,936 B2 * | 5/2020 | Schreiber ............... | C07K 14/00 |
| 2016/0177276 A1 * | 6/2016 | Lo ........................ | C07K 16/2887 424/134.1 |
| 2017/0095531 A1 * | 4/2017 | Schreiber ............... | C07K 19/00 |
| 2018/0064787 A1 * | 3/2018 | Schreiber ............... | A61P 35/00 |
| 2018/0125935 A1 * | 5/2018 | Schreiber ............... | A61P 35/00 |
| 2018/0141986 A1 * | 5/2018 | Tian ........................ | A61P 35/00 |
| 2018/0326004 A1 * | 11/2018 | Schreiber ............... | A61P 35/00 |
| 2018/0326005 A1 * | 11/2018 | Schreiber ............... | A61P 37/04 |
| 2018/0326006 A1 * | 11/2018 | Schreiber ............... | A61P 37/06 |
| 2018/0326007 A1 * | 11/2018 | Schreiber ............... | A61P 37/04 |
| 2018/0326008 A1 * | 11/2018 | Schreiber ........... | A61K 38/1774 |
| 2019/0151413 A1 * | 5/2019 | Schreiber ............... | C07K 19/00 |
| 2019/0365717 A1 * | 12/2019 | Raaben ................ | C07K 16/468 |
| 2019/0373867 A1 * | 12/2019 | Shen .................... | A01K 67/0278 |
| 2020/0071380 A1 * | 3/2020 | Schreiber ........... | C07K 14/70578 |
| 2020/0101136 A1 * | 4/2020 | Schreiber ............... | A61P 37/02 |
| 2020/0172623 A1 * | 6/2020 | Tian ........................ | A61P 35/00 |

OTHER PUBLICATIONS

Petrova et al. (Clin Cancer Res; 23(4):1068-1079 (Feb. 15, 2017); Published OnlineFirst Nov. 17, 2016)).*

* cited by examiner

*Primary Examiner* — Lynn A Bristol
(74) *Attorney, Agent, or Firm* — Duane Morris LLP; Thomas J. Kowalski; Deborah L. Lu

(57) ABSTRACT

The present invention provides a recombinant fusion protein containing an anti-PD-L1 antibody, with at least one paratope of the anti-PD-L1 antibody linked via a linker to an extracellular Ig-like domain of a signal-regulator protein (SIRP) at N-terminus of a heavy chain or a light chain, wherein the recombinant fusion protein can bind to CD47, PD-L1 and FcR simultaneously. The present invention also provides a polynucleotide encoding the recombinant fusion protein, an expression vector containing the polynucleotide, a method for producing the recombinant protein and a method for treating a disease caused by over expression of CD47 and/or PD-L1 using the recombinant protein.

8 Claims, 7 Drawing Sheets

Specification includes a Sequence Listing.

SEQ ID NO: 5

```
GAGGTGCAGC TGGTGGAGTC TGGGGGAGGC CTGGTTCAAC CGGCGGGAG CCTGCGGCTC   60
AGCTGCGCCG CATCGGATT CACCTTTCT GATTCTTGGA TCCACTGGGT TCGCCAGGCC  120
CCTGGAAACG GACTGGAGTG GGTTGCCTGG ATCTCCCCAT ATGGTGGCTC GACTTATTAT  180
GCCGACTCTG TGAAGGACG GTTTACTATC TCCGCGGACA CTAGCAAAA TACCGCATAC  240
CTGCAGATGA ACTCTCTCCG CGCTGAAGAT ACAGCTGTGT ACTACTGCGC AAGACGTCAC  300
TGGCCGGGCG GATTCGACTA TTGGGGCCAG GGCACTCTGG TCACGGTGTC CTCCGCGAGC  360
ACCAAGGGCC CATCGGTCTT CCCCCTGGCA CCTCCTCCA AGAGCACCTC TGGGGCACA  420
GCGGCCCTGG GCTGCCTGGT CAAGGACTAC TTCCCGGAAC CGGTGACGGT GTCGTGGAAC  480
TCAGGCGCCC TGACCAGCGG CGTGCACACC TTCCCGGCTG TCCTACAGTC CTCAGGACTC  540
TACTCCCTCA GCAGCGTGGT GACCGTGCCC TCCAGCAGCT TGGGCACCCA GACCTACATC  600
TGCAACGTGA ATCACAAGCC CAGCAACACC AAGGTGGACA AGAGAGTTGA GCCCAAATCT  660
TGTGACAAAA CTCACACATG CCCACCGTGC CCAGCACCTG AACTCCTGG GGGACCGTCA  720
GTCTTCCTCT TCCCCCCAAA ACCCAAGGAC ACCCTCATGA TCTCCCGGAC CCCTGAGGTC  780
ACATGCGTGG TGGTGGACGT GAGCCACGAA GACCCTGAGG TCAAGTTCAA CTGGTATGTG  840
GACGGCGTGG AGGTGCATAA TGCCAAGACA AAGCCGCGGG AGGAGCAGTA CAACGCCACG  900
TACCGTGTGG TCAGCGTCCT CACCGTCCTG CACCAAGACT GGCTGAATGG CAAGGAGTAC  960
AAGTGCAAGG TCTCCAACAA AGCCCTCCCA GCCCCCATCG CCGCAACCAT CTCCAAAGCC 1020
AAAGGGCAGC CCCGAGAACC ACAGGTGTAC ACCCTGCCCC CATCCCGGGA GGAGATGACC 1080
AAGAACCAAG TCAGCCTGAC CTGCCTGGTC AAAGGCTTCT ATCCCAGCGA CATCGCCGTG 1140
GAGTGGGAGA GCAATGGGCA GCCGGAGAAC AACTACAAGA CCACGCCTCC CGTGCTGGAC 1200
TCCGACGGCT CCTTCTTCCT CTATTCCAAG CTCACCGTGG ACAAGAGCAG GTGGCAGCAG 1260
GGGAACGTCT TCTCATGCTC CGTGATGCAT GAGGCTCTGC ACAACCACTA CACGCAGAAG 1320
AGCCTCTCCC TGTCTCCGGG CAAATGA                                    1347
```

FIG. 3

SEQ ID NO: 6

```
EVQLVESGGGLVQPGGSLRLSCAASGFTFSDSWIHWVRQAPGKGLEWVAWISPYGGSTYY    60
ADSVKGRFTISADTSKNTAYLQMNSLRAEDTAVYYCARRHWPGGFDYWGQGTLVTVSSAS   120
TKGPSVFPLAPSSKSTSGGTAALGCLVKDYFPEPVTVSWNSGALTSGVHTFPAVLQSSGL   180
YSLSSVVTVPSSSLGTQTYICNVNHKPSNTKVDKRVEPKSCDKTHTCPPCPAPELLGGPS   240
VFLFPPKPKDTLMISRTPEVTCVVVDVSHEDPEVKFNWYVDGVEVHNAKTKPREEQYNAT   300
YRVVSVLTVLHQDWLNGKEYKCKVSNKALPAPIAATISKAKGQPREPQVYTLPPSREEMT   360
KNQVSLTCLVKGFYPSDIAVEWESNGQPENNYKTTPPVLDSDGSFFLYSKLTVDKSRWQQ   420
GNVFSCSVMHEALHNHYTQKSLSLSPGK                                   448
```

FIG. 4

SEQ ID NO: 7

```
GATATTCAAA TGACACAAAG CCCTTCTTCC CTGAGCGCTT CTGTGGGCGA CCGCGTTACA  60
ATCACATGCA GGGCAAGCCA GGATGTCAGC ACTGCTGTCG CTTGGTACCA GCAGAAACCA 120
GGCAAGGCAC CTAAGCTCCT GATCTACTCC GCCTCCTTCC TGTATTCCGG AGTCCCCTCC 180
CGGTTTTCCG GCTCCGGGTC TGGGACCGAT TTCACCCTGA CCATCAGCTC CCTCCAGCCT 240
GAAGATTTCG CCACCTATTA TTGTCAGCAG TACCTCTATC ACCCAGCGAC CTTTGGCCAG 300
GGGACAAAAG TGGAGATCAA GCGAACTGTG GCTGCACCAT CTGTCTTCAT CTTCCCGCCA 360
TCTGATGAGC AGTTGAAATC TGGAACTGCC TCTGTTGTGT GCCTGCTGAA TAACTTCTAT 420
CCCAGAGAGG CCAAAGTACA GTGGAAGGTG GATAACGCCC TCCAATCGGG TAACTCCCAG 480
GAGAGTGTCA CAGAGCAGGA CAGCAAGGAC AGCACCTACA GCCTCAGCAG CACCCTGACG 540
CTGAGCAAAG CAGACTACGA GAAACACAAA GTCTACGCCT GCGAAGTCAC CCATCAGGGC 600
CTGAGCTCGC CCGTCACAAA GAGCTTCAAC AGGGGAGAGT GTTAG         645
```

FIG. 5

SEQ ID NO: 8

```
DIQMTQSPSSLSASVGDRVTITCRASQDVSTAVAWYQQKPGKAPKLLIYSASFLYSGVPS  60
RFSGSGSGTDFTLTISSLQPEDFATYYCQQYLYHPATFGQGTKVEIKRTVAAPSVFIFPP 120
SDEQLKSGTASVVCLLNNFYPREAKVQWKVDNALQSGNSQESVTEQDSKDSTYSLSSTLT 180
LSKADYEKHKVYACEVTHQGLSSPVTKSFNRGEC                           214
```

FIG. 6

RECOMBINANT FUSION PROTEIN CONTAINING AN ANTI-PD-L1 ANTIBODY

INCORPORATION BY REFERENCE

This application claims benefit of and priority to U.S. provisional patent application Ser. No. 62/577,704 filed Oct. 26, 2017.

SEQUENCE STATEMENT

The instant application contains a Sequence Listing, which has been submitted electronically and is hereby incorporated by reference in its entirety. Said ASCII copy, is named SequenceListing.txt and is 25.22 kb in size.

FIELD OF THE INVENTION

The invention relates to a recombinant fusion protein, preparation and use thereof, especially its use in tumor therapies.

BACKGROUND OF THE INVENTION

Cancer cells have developed several mechanisms to evade a host's immune surveillance, including: 1) Evasion of immune surveillance by T-lymphocytes, by high expression of membrane protein PD-L1 and PD-L2, both of which bind to PD-1 on the surface of T-cell, inducing T-cell apoptosis; 2) Evasion of immune surveillance by natural killer (NK) cells; the NKG2D protein on the surface of NK cells, upon binding to the MICA/MICB proteins on the surface of the cancer cells, can activate NK cells to kill the cancer cells; however, cancer cells have developed a mechanism that promotes the detachment of MICA/MICB from the cell membranes; the detached MICA/MICB binds to the NKG2D, blocking its activation of the NK cells; 3) Evasion of the immune surveillance by macrophages (Mφ); almost all cancer cells express on their surfaces a high level of CD47, which binds to the signal regulatory protein alpha (SIRPα) on the surface of Mφ, thereby inducing the production of an inhibitory signal, which inhibits the phagocytosis of cancer cells by Mφ. It can be seen that the cancer cells are quite "smart" and reproduce quickly depending on their developed evasion mechanisms. Accordingly, development of effective anti-cancer drugs for killing all the cancer cells needs to target these mechanisms.

SIRP and CD47

Signal regulatory protein (SIRP) is a trans-membrane glycoprotein, including three family members, SIRPα (CD172a), SIRPβ (CD172b) and SIRPγ (CD172g). All three proteins comprise similar extracellular regions but distinct intracellular domains. The extracellular region contains three immunoglobulin-like domains, one Ig V-set and two Ig C-set domains. The intracellular domain of SIRPα (CD172a) contains two inhibitory signaling regions that can inhibit signal transduction and corresponding cell functions. SIRPβ (CD172b) and SIRPγ (CD172g) have very short intracellular regions without any signal transduction domain. However, SIRPβ (CD172b) may function through an adaptor protein, e.g., DAP12 for signal transduction. SIRPs are mainly expressed in macrophages (Mφ), dendritic cells (DCs) and neurons.

CD47 is a transmembrane glycoprotein belonging to the immunoglobulin superfamily, and is expressed on the surface of all cell types including red blood cells. Ligands for CD47 include integrins, thrombospondin-1 and SIRPs. CD47, by interacting with SIRPα to emit a 'don't eat me' signal, can inhibit the phagocytosis by macrophages and thus protects cells, such as blood cells, from being attacked by macrophages.

Studies have shown that many tumor or cancer cells over-express CD47, which, by binding to the SIRPα on the cell surface of macrophages, prevent phagocytosis of the cancer cells by macrophages. Cancer cells that over-express CD47 include cells of acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, and pancreatic cancer. It is reported that injection of CD-47 specific antibody that blocks the binding of CD47 to SIRPα can significantly inhibit tumor growth in tumor-bearing mice. Tumor or cancer cells were eliminated completely when the same antibody was injected into the mice carrying human leukemia cells (Theocharides A P A, et al., 2012).

PD-L1 and PD-1

PD-L1, also known as programmed death-ligand 1 or CD274, is a transmembrane protein that plays a major role in suppressing the immune system during some particular events such as tissue allografts, autoimmune disease and cancer development. In cancers, loss of feedback restriction between transcription factors like STAT3 and NF-κB can lead to increased local PD-L1 expression, which could limit the effectiveness of systemic treatment with agents targeting PD-L1 (Vlahopoulos SA, 2017). An analysis of 196 tumor specimens from patients with renal cell carcinoma found that high tumor expression of PD-L1 was associated with increased tumor aggressiveness and a 4.5-fold increased risk of death (Thompson R H et al., 2004).

PD-1 is a cell surface receptor of about 268 amino acids. When bound with PD-L1 or PD-L2, it down-regulates the immune system and promotes self-tolerance by suppressing T cell inflammatory activity. The inhibitory effect of PD-1 on immune system prevents autoimmune diseases but also prevent the immune system from killing cancer cells. An anti-PD-1 antibody, BMS-936558, produced objective responses in approximately one in five to one in four patients with non-small-cell lung cancer, melanoma, or renal-cell cancer (Suzanne L. Topalian et al., 2012).

Fc and FcR

The fragment crystallizable region (Fc region) is the tail region of an antibody and is the domain that determines the effector function of the antibody, that is, how it engages with specific cell receptors or other defense proteins.

An Fc receptor (FcR) is a protein found on the surface of certain cells, including B lymphocytes, follicular dendritic cells, natural killer cells, macrophages, neutrophils, eosinophils, basophils, and mast cells. These cells contribute to the protective functions of the immune system.

An Fc region may interact with Fc receptors and some proteins of the complement system, which activates the immune system.

Therapeutic Bi-Specific or Multi-Specific Fusion Proteins/Antibodies

Antibodies targeting a single tumor-associated antigen have been found to have limited therapeutic efficacy. For example, the overall response rate of a currently approved anti-PD-L1 antibody, Avelumab (BAVENCIO), is only 33%.

Therefore, some anti-cancer drugs have been or are being developed against two or more targets, but most of the currently available technologies involving bi-specific or multi-specific antibodies, including Triomab, CrossMab, DVD-Ig, BiTE, DART and TandAb, have drawbacks such as high level of aggregation, large molecular weight (>200 kDa) and short half-life (<12 hrs, BiTE, DART and TandAb), reducing their therapeutic efficacy.

WO2016/169261 discloses a recombinant bi-functional fusion protein of about 90 kDa, targeting both CD47 and FcR, which was used to treat Balb/c nude mice carrying HL cells, and an enhanced anti-tumor effect was observed. However, there is no report so far of any single molecule drug that accurately targets CD47, PD-L1 and FcR at the same time and is of a low molecular weight and a long half-life, and the present invention satisfies this need.

SUMMARY OF THE INVENTION

The present invention discloses a recombinant fusion protein, comprising an anti-PD-L1 antibody, with at least one paratope of the anti-PD-L1 antibody linked via a linker to an extracellular Ig-like domain of a signal-regulator protein (SIRP) at the N-terminus of a heavy chain or a light chain constituting the paratope, wherein the protein can bind to CD47, PD-L1 and FcR simultaneously. Binding to CD47 on cancer cells blocks the interaction of CD47 with SIRPs on macrophages and thus releases the check on macrophages by SIRP-mediated inhibitory signals; while binding to PD-L1 on cancer cells releases the check on T cells by PD-1-mediated inhibitory signals; and at the same time, binding to FcRs on NK cells or macrophages stimulates targeted cancer cell killings by NK cells or macrophages.

In an embodiment, one paratope of the anti-PD-L1 antibody is linked via a linker to an extracellular Ig-like domain of a signal-regulator protein (SIRP) at the N-terminus of a heavy chain or a light chain constituting the paratope. In another embodiment, each paratope of the anti-PD-L1 antibody is linked via a linker to an extracellular Ig-like domain of a signal-regulator protein (SIRP) at the N-terminus of a heavy chain or a light chain constituting the paratope. In one embodiment, each paratope of the anti-PD-L1 antibody is linked via a linker to an extracellular Ig-like domain of a signal-regulator protein (SIRP) at the N-terminus of a heavy chain constituting the paratope. In one embodiment, each paratope of the anti-PD-L1 antibody is linked via a linker to an extracellular Ig-like domain of a signal-regulator protein (SIRP) at the N-terminus of a light chain constituting the paratope. In a further embodiment, one paratope of the anti-PD-L1 antibody is linked via a linker to an extracellular Ig-like domain of a signal-regulator protein (SIRP) at the N-terminus of a heavy chain constituting the paratope, and the other paratope of the anti-PD-L1 antibody is linked via a linker to an extracellular Ig-like domain of a signal-regulator protein (SIRP) at the N-terminus of a light chain constituting the paratope. In some embodiments, each paratope is linked to more than one extracellular Ig-like domains of a signal-regulator protein (SIRP) at the N-terminus of a heavy chain and a light chain constituting the paratope.

In one embodiment, the signal-regulatory protein in the recombinant fusion protein may be SIRPα, and the extracellular Ig-like domain of the signal-regulatory protein may be the first extracellular Ig-like domain of SIRPα (SIRPαD1). The extracellular Ig-like domain of the signal-regulatory protein, such as SIRPαD1, can bind to CD47 on the cell surfaces of, for instance, cancer/tumor cells and thus block the interaction of CD47 with SIRPs on the cell surfaces of macrophages.

In one embodiment, the SIRPαD1 has the nucleic acid sequence and amino acid sequence set forth in SEQ ID NOs: 1 and 2, respectively. In some embodiments, the SIRPαD1 may comprise an amino acid sequence having at least 80%, 85%, 90%, 95%, 98% or 99% identity to SEQ ID NO: 2, wherein the SIRPαD1 can bind to CD47 on the cell surfaces of, for example, cancer/tumor cells and block the interaction of CD47 with SIRPs on the cell surfaces of macrophages.

The linker in the recombinant fusion protein may be a peptide of about 5 to 30 amino acid residues. In an embodiment, the linker is a peptide of 10 to 30 amino acid residues. In another embodiment, the linker is a peptide of 15 to 30 amino acid residues. In some embodiments, the linker is -(Gly-Gly-Gly-Gly-Ser)$_3$- (SEQ ID NO: 4), which may be encoded by SEQ ID NO: 3.

The anti-PD-L1 antibody may be an isolated monoclonal antibody such as Atezolizumab, Avelumab, Durvalumab, and antibodies having at least 80%, 85%, 90%, 95%, 98% or 99% amino acid identity to Atezolizumab, Avelumab, or Durvalumab.

The anti-PD-L1 antibody may be an isolated monoclonal antibody, comprising two heavy chains each having an amino acid sequence of SEQ ID NO: 6, and two light chains each having an amino acid sequence of SEQ ID NO: 8, which two may be encoded by nucleic acid sequences of SEQ ID NOs: 5 and 7, respectively. The antigen-binding (Fab) portion (or paratope) of the anti-PD-L1 antibody can bind to PD-L1 on the cell surfaces of cancer/tumor cells to block the interaction of PD-L1 with PD-1 on the cell surfaces of T cells and thus release the check on T cells by PD-1-mediated inhibitory signals, while the Fc portion of the anti-PD-L1 antibody can bind to FcRs on the cell surfaces of NK cells or macrophages to stimulate cancer cell killings by the NK cells or macrophages. In some embodiments, the heavy chain may comprise an amino acid sequence having at least 80%, 85%, 90%, 95%, 98% or 99% identity to SEQ ID NO: 6, wherein the anti-PD-L1 antibody is able to bind to PD-L1 and block the interaction of PD-L1 with PD-1 on the cell surfaces of T cells, and is also able to bind to FcRs on the cell surfaces of NK cells or macrophages and thus activate the NK cells or macrophages for killing the cancer cells. In some embodiments, the light chain may comprise an amino acid sequence having at least 80%, 85%, 90%, 95%, 98% or 99% identity to SEQ ID NO: 8, wherein the anti-PD-L1 antibody is able to bind to PD-L1 and block the interaction of PD-L1 with PD-1 on the cell surfaces of T cells.

The SIRPαD1-Linker-anti-PD-L1 heavy chain comprises an amino acid sequence of SEQ ID NO: 10, which may be encoded by nucleotide of SEQ ID NO: 9. In some embodiments, the SIRPαD1-Linker-anti-PD-L1 heavy chain comprises an amino acid sequence having at least 80%, 85%, 90%, 95%, 98% or 99% identity to SEQ ID NO: 10, wherein the SIRPαD1-Linker-anti-PD-L1 heavy chain together with the light chain of the anti-PD-L1 antibody can bind to CD47, PD-L1 and FcR, i) blocking the interaction of PD-L1 on cancer cells with PD-1 on T cells; ii) blocking the interaction of CD47 on cancer cells with SIRPs on macrophages; and iii) stimulating cancer cell killings by NK cells or macrophages.

A nucleic acid molecule encoding the recombinant fusion protein of the present invention is also provided, as well as an expression vector comprising the nucleic acid and a host cell comprising the expression vector.

A method for preparing the recombinant fusion protein using the host cell comprising the expression vector is also provided, and comprises steps of (i) expressing the recombinant fusion protein in the host cell and (ii) isolating the recombinant fusion protein from the host cell.

In another respect, the present invention provides a pharmaceutical composition, comprising the recombinant fusion protein of the present invention, and at least one pharmaceutically acceptable carrier. The pharmaceutical composition may further comprise at least one adjuvant.

In another aspect, the present invention provides a method for treating a disease caused by over-expression of CD47 and/or PD-L1, comprising administering to a patient or a subject in need thereof a therapeutically effective amount of the pharmaceutical composition of the present invention.

In one embodiment, the present invention provides the use of the recombinant fusion protein in the manufacture of a pharmaceutical composition for the treatment of a disease caused by over-expression of CD47 and/or PD-L1.

In one embodiment, the method of the present invention is for treating a disease selected from the group consisting of acute myelocytic leukemia (AML), chronic myelocytic leukemia (CML), acute lymphoblastic leukemia (ALL), non-Hodgkin's lymphoma (NHL), multiple myeloma (MM), bladder cancer, ovarian cancer, prostate cancer, lung cancer, colon cancer, breast cancer, pancreatic cancer, and renal cell carcinoma. In one embodiment, the present invention provides a method for treating Crohn's disease, allergic asthma or rheumatoid arthritis.

Other features and advantages of the instant disclosure will be apparent from the following detailed description and examples, which should not be construed as limiting. The contents of all references, Genbank entries, patents and published patent applications cited throughout this application are expressly incorporated herein by reference.

DESCRIPTION OF THE DRAWINGS

FIG. 3 shows the nucleic acid sequence of a heavy chain of an anti-PD-L1 antibody (SEQ ID NO: 5) in the recombinant fusion protein IMM2505.

FIG. 4 shows the amino acid sequence of a heavy chain of an anti-PD-L1 antibody (SEQ ID NO: 6) in the recombinant fusion protein IMM2505.

FIG. 5 shows the nucleic acid sequence of a light chain of an anti-PD-L1 antibody (SEQ ID NO: 7) in the recombinant fusion protein IMM2505.

FIG. 6 shows the amino acid sequence of a light chain of an anti-PD-L1 antibody (SEQ ID NO: 8) in the recombinant fusion protein IMM2505.

DETAILED DESCRIPTION OF THE INVENTION

Figure 1:
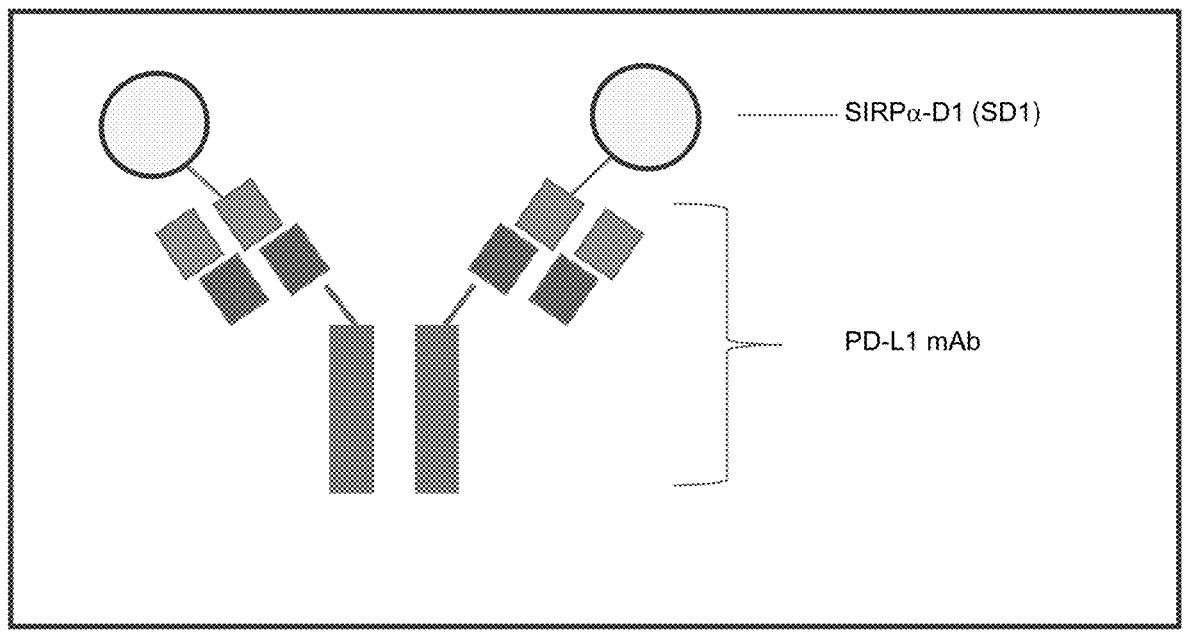
FIG. 1 is a schematic diagram of the structure of the recombinant fusion protein of the present invention.
Figure 2:
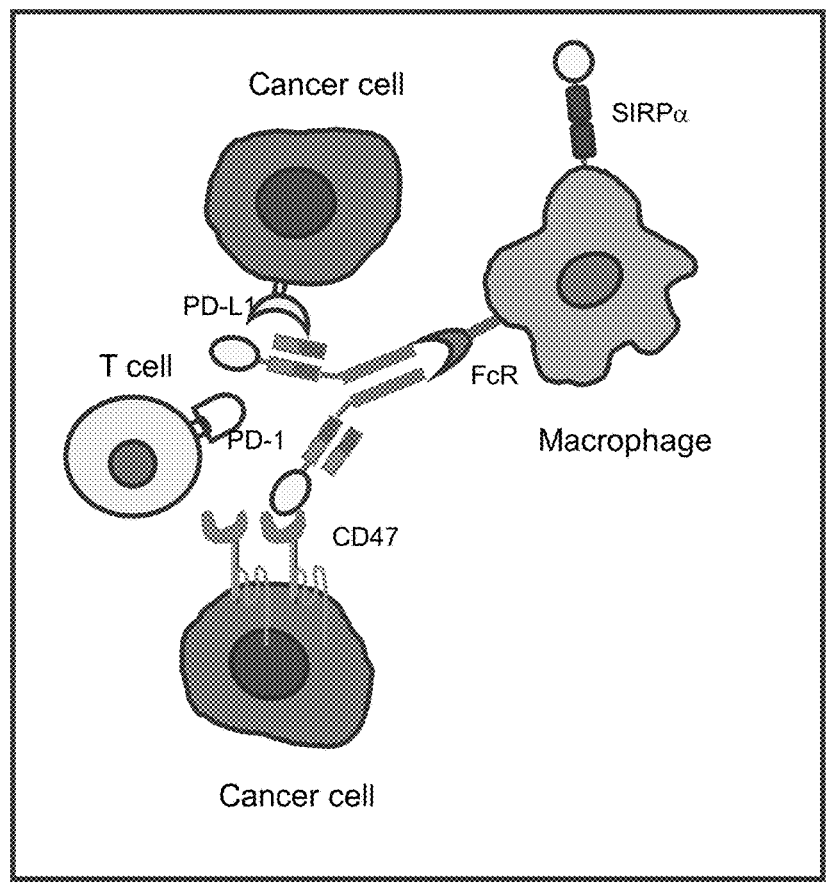
FIG. 2 is a schematic diagram showing action mechanism of the recombinant fusion protein of the present invention.

There are principally three different approaches to targeting two or more pharmacologies of tumor growth. Most commonly, patients can be given a cocktail of two or more different drugs. Although this option allows for maximal flexibility with respect to possible drug combinations and different dosages, it suffers from (a) potentially poor adherence to treatment by the patient because of the increased pill burden and the different dosing schedules for the individual drugs, (b) possible incompatibilities because of drug-drug interactions, and (c) increased risk of drug side effects. These problems can reduce the effectiveness of therapy and hamper the attainment of treatment goals particularly in the management of chronic diseases such as cancer.

The second approach relies on the use of fixed-dose combinations of drugs in a single dosage form. This approach reduces pill burden, resulting in improved patient compliance. The disadvantage of fixed-dose combinations is primarily the limited choice of possible dose ratios between the active ingredients, which makes it more difficult to properly titrate the individual patient to maximum efficacy with minimal adverse effects. In addition, different pharmacokinetic properties of the components in the combination might lead to a complex temporal mismatch in pharmacodynamic effects at the individual targets thereby compromising overall efficacy.

The third approach is the use of multifunctional drugs that combine two or more pharmacologies in a single compound. The design and validation of such multifunctional molecules are more complex and require substantial investigation into the optimal ratio of target activities in the molecule, but the unified pharmacokinetics may yield matched pharmacodynamic activities at the molecular targets. Multifunctional molecules may also be amenable to fixed dose combination with other drugs thereby combining three or even four pharmacologies in a single pill to produce further increments in efficacy.

Through diligent experimentation, the present inventor has invented a novel recombinant multi-functional fusion protein, which can attack tumors, via three mechanisms of actions, one to release the check or inhibition on T cells by PD-1-mediated inhibitory signals, one to release the check on macrophages by SIRP-mediated inhibitory signals, another to stimulate cancer cell killings by NK cells and/or macrophages.

The recombinant fusion protein of the present invention comprises an anti-PD-L1 antibody, with at least one paratope of the anti-PD-L1 antibody linked via a linker to an extracellular Ig-like domain of a signal-regulator protein (SIRP) at the N-terminus of a heavy chain or a light chain constituting the paratope. The recombinant protein can bind to CD47, HER2 and FcR simultaneously, i) blocking the interaction of PD-L1 on cancer cells with PD-1 on T cells and thus releasing the check on T cells by PD-1-mediated inhibitory signals; ii) blocking the interaction of CD47 on cancer cells with SIRPs on macrophages and thus releasing the check on macrophages by SIRP-mediated inhibitory signals; and iii) binding Fc portion of the antibody to FcRs on NK cells or macrophages to stimulate cancer cell killings by NK cells or macrophages. In an embodiment, one paratope of the anti-PD-L1 antibody is linked via a linker to an extracellular Ig-like domain of a signal-regulator protein (SIRP) at the N-terminus of a heavy chain or a light chain constituting the paratope. In another embodiment, each paratope of the anti-PD-L1 antibody is linked via a linker to an extracellular Ig-like domain of a signal-regulator protein (SIRP) at the N-terminus of a heavy chain or a light chain constituting the paratope. In one embodiment, each paratope of the anti-PD-L1 antibody is linked via a linker to an extracellular Ig-like domain of a signal-regulator protein (SIRP) at the N-terminus of a heavy chain constituting the paratope. In one embodiment, each paratope of the anti-PD-L1 antibody is linked via a linker to an extracellular Ig-like domain of a signal-regulator protein (SIRP) at the N-terminus of a light chain constituting the paratope. In a further embodiment, one paratope of the anti-PD-L1 antibody is linked via a linker to an extracellular Ig-like domain of a signal-regulator protein (SIRP) at the N-terminus of a heavy chain constituting the paratope, and the other paratope of the anti-PD-L1 antibody is linked via a linker to an extracellular Ig-like domain of a signal-regulator protein (SIRP) at the N-terminus of a light chain constituting the paratope. In some embodiments, each paratope is linked to more than one (for instance, two) extracellular Ig-like domain of a signal-regulator protein (SIRP) at the N-terminus of a heavy chain and a light chain constituting the paratope. The recombinant fusion protein of the present invention is small in size (150-180 kDa) and has a long half-life of 5-10 days.

The three main components contained in the fusion protein of the present invention are the extracellular Ig-like domain of a signal-regulator protein (SIRP), the linker, and the anti-PD-L1 antibody. A person of ordinary skills in the art will recognize that there are many design choices for selecting the above three components. Preferably, human-derived sequence is used in human cancer therapies, as the strong immunogenicity of the proteins or peptides from non-human animals may lead to allergy and other adverse effects. However, other animal proteins or peptides, humanized if appropriate, may also be used in the present invention based on different application purposes.

Any extracellular Ig-like domain of any SIPR (SIRPα, SIRPβ, and SIRPγ) capable of binding with CD47 may be selected for construction of the fusion protein. In one embodiment, the signal-regulatory protein in the recombinant fusion protein is SIRPα, and the extracellular Ig-like domain of the signal-regulatory protein is the first extracellular Ig-like domain of SIRPα (SIRPαD1).

In one embodiment, the recombinant fusion protein comprises SIRPαD1 having the nucleic acid sequence and amino acid sequence set forth in SEQ ID Nos: 1 and 2, respectively. In another embodiment, the SIRPαD1 may comprise an amino acid sequence having at least 80%, 85%, 90%, 95%, 98% or 99% identity to SEQ ID NO: 2, wherein the SIRPαD1 can bind to CD47 on the cell surface of cancer/tumor cells and block the interaction of CD47 with SIRPs on the cell surfaces of macrophages.

Linkers serve primarily as a spacer between the extracellular Ig-like domain of SIRP and the N-terminus of the heavy chain of an anti-PD-L1 antibody. The linker may be made up of amino acids linked together by peptide bonds, preferably from 5 to 30 amino acids linked by peptide bonds, wherein the amino acids are selected from the 20 naturally occurring amino acids. One or more of these amino acids may be glycosylated, as is understood by those of skill in the art. In one embodiment, the 5 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines (particularly (Glys, $(Gly)_8$, poly(Gly-Ala), and polyalanines. One exemplary suitable linker as shown in the Examples below is (Gly-Ser), such as -(Gly-Gly-Gly-Gly-Ser)$_3$- (SEQ ID NO: 4).

Linkers may also be non-peptide linkers. For example, alkyl linkers such as —NH—, —(CH$_2$)s-C(O)—, wherein s=2-20 can be used. These alkyl linkers may further be substituted by any non-sterically hindering group such as lower alkyl (e.g., $C_{1-4}$) lower acyl, halogen (e.g., CI, Br), CN, NH$_2$, phenyl, etc.

Any anti-PD-L1 antibody may be used in the formation of the fusion protein of the present invention. The anti-PD-L1 antibody may be an isolated monoclonal antibody selected from the group consisting of Atezolizumab, Avelumab, and Durvalumab.

In some embodiments, the anti-PD-L1 antibody is an isolated monoclonal antibody comprising two heavy chains each having an amino acid sequence of SEQ ID NO: 6, and two light chains each having an amino acid sequence of SEQ ID NO: 8, which two may be encoded by nucleic acid sequences of SEQ ID NOs: 5 and 7, respectively. The Fab portion (or paratope) of the anti-PD-L1 antibody can bind to PD-L1 on the cell surfaces of cancer/tumor cells to block the interaction of PD-L1 with PD-1 on the cell surfaces of T cells and thus release the check on T cells by PD-1-mediated inhibitory signals, while the Fc portion of the anti-PD-L1 antibody can bind to FcRs on the cell surfaces of NK cells or macrophages to stimulate cancer cell killings by the NK cells or macrophages. In some embodiments, the heavy chain may comprise an amino acid sequence having at least 80%, 85%, 90%, 95%, 98% or 99% identity to SEQ ID NO: 6, wherein the anti-PD-L1 antibody is able to bind to PD-L1 and block the interaction of PD-L1 with PD-1 on the cell surfaces of T cells, and is also able to bind to FcRs on the cell surfaces of NK cells or macrophages and thus activate the NK cells or macrophages for killing the cancer cells. In some embodiments, the light chain may comprise an amino acid sequence having at least 80%, 85%, 90%, 95%, 98% or 99% identity to SEQ ID NO: 8, wherein the anti-PD-L1 antibody is able to bind to PD-L1 and block the interaction of PD-L1 with PD-1 on the cell surfaces of T cells.

Also, the present invention provides a polynucleotide molecule encoding the recombinant fusion protein and an expression vector expressing the recombinant bi-functional fusion protein. Examples of vectors include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

The present invention provides host cells comprising the above expression vectors. The host cells may be transformed or transfected with the expression vectors. Suitable host cells include *Escherichia coli*, yeasts and other eukaryotes. Preferably, *Escherichia coli*, yeast or mammalian cell lines (such as COS or CHO) are used.

In another aspect, the present disclosure provides a pharmaceutical composition comprising the fusion protein of the present invention formulated together with a pharmaceutically acceptable adjuvant. The composition may optionally contain one or more additional pharmaceutically active ingredients, such as another antibody or a drug. The pharmaceutical compositions of the invention also can be administered in a combination therapy with, for example, another immune-stimulatory agent, anti-cancer agent, an anti-viral agent, or a vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington:

The Science and Practice of Pharmacy, 20th Ed. (Lippincott Williams & Wilkins 2003), the disclosure of which is incorporated herein by reference.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in injection. For example, the vehicle or carrier may be neutral buffered saline or saline mixed with serum albumin. Other exemplary pharmaceutical compositions comprise Tris buffers, or acetate buffers, which may further include sorbitol or a suitable substitute thereof. In one embodiment of the present invention, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

Preferably, the pharmaceutical composition is suitable for intravenous, intramuscular, subcutaneous, parenteral, spinal or epidermal administration (e.g., by injection or infusion). Depending on the route of administration, the active molecule can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, the fusion protein can be administered as a sustained release formulation, in which case less frequent administration is required.

For administration of the fusion protein, the dosage ranges from about 0.0001 to 100 mg/kg, and more usually 0.01 to 10 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration twice per week, once per week, once every two weeks, once every three weeks, once every four weeks, once a month, once every 3 months or once every three to 6 months. Preferred dosage regimens for the fusion protein of the invention include 3 mg/kg body weight or 6 mg/kg body weight via intraperitoneal administration, with the antibody being given using one of the following dosing schedules: (i) every four weeks for six dosages, then every three months; (ii) every three weeks; (iii) 3 mg/kg body weight once followed by 1 mg/kg body weight every three weeks; (vi) 6 mg/kg body weight, one dosage per week. In some methods, dosage is adjusted to achieve a plasma antibody concentration of about 1-1000 µg/ml and in some methods about 25-300 µg/ml.

A "therapeutically effective dosage" of a fusion protein of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 40%, more preferably by at least about 60%, even more preferably by at least about 80%, and still more preferably by at least about 99% relative to untreated subjects. A therapeutically effective amount of a fusion protein of the present invention can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the fusion protein of the invention can be formulated to ensure proper distribution in vivo. For example, to ensure that the therapeutic fusion proteins of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331.

A gene therapy in vivo is also envisioned wherein a nucleic acid molecule encoding the recombinant fusion protein of the present invention, or a derivative thereof is introduced directly into the subject. For example, a nucleic acid sequence encoding a recombinant fusion protein of the present invention is introduced into target cells via local injection of a nucleic acid construct with or without an appropriate delivery vector, such as an adeno-associated virus vector. Alternative viral vectors include, but are not limited to, retroviruses, adenovirus, herpes simplex vims and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present invention is to provide a method for preparing the above recombinant fusion protein and the pharmaceutical composition comprising the same. In one embodiment, the method comprises (1) providing an protein-encoding polynucleotide molecule; (2) constructing an expression vector comprising the polynucleotide molecule of (1); (3) transfecting or transforming suitable host cells with the expression vector of (2) and cultivating the host cells to express the protein; and (4) purifying the protein. The preparation may be carried out with well-known technologies by an ordinarily skilled artisan.

Another object of the present invention is to provide a method of treating cancer using the pharmaceutical composition of the present invention, comprising administrating an effective amount of the aforementioned pharmaceutical composition to the patients or subjects in need thereof. In one embodiment, the pharmaceutical composition is used to treat CD47 and/or PD-L1-overexpressing tumors or cancers, including but not limited to acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, pancreatic cancer and renal cancer.

In one embodiment, the diseases related to over-expressions of CD47 and/or PD-L1 include, but are not limited to, Crohn's disease, allergic asthma, and rheumatoid arthritis.

The present invention is now further described with the non-limiting examples below.

EXAMPLES

In the examples below, IMM25 is a monoclonal anti-PD-L1 antibody that targets PD-L1. This antibody has two heavy chains each having an amino acid sequence of SEQ ID NO: 6, and two light chains each having an amino acid sequence of SEQ ID NO: 8, which two may be encoded by nucleic acid sequences of SEQ ID NOs: 5 and 7, respectively.

IMM01 is a fusion protein capable of binding to CD47, consisting of SIRPαD1 linked to an Fc fragment, which was described in WO2016169261. The nucleic acid sequence and amino acid sequence of this fusion protein are set forth in SEQ ID NO: 11 and SEQ ID NO: 12, respectively.

IMM2505 is a recombinant fusion protein, containing two SIRPαD1s each linked via a GS-linker, to IMM25 at the N-terminus of each heavy chain, wherein the SIRPαD1 has an nucleic acid sequence and amino acid sequence of SEQ ID NO: 1 and SEQ ID NO: 2, respectively, and the linker having an amino acid sequence of SEQ ID NO: 4 can be encoded by the nucleic acid sequence of SEQ ID NO: 3.

Example 1. Construction of Vectors Expressing IMM2505

Full length coding sequence of recombinant fusion protein IMM2505 was designed artificially. Specifically, for the heavy chain, the coding sequence of the first extracellular domain of SIRPα (SIRPαD1) (SEQ ID NO: 1) was linked through the GS-linker (SEQ ID NO: 3) to the N terminal of the heavy chain variable region coding sequence of IMM25 (SEQ ID NO:5). 57 nucleotides encoding the signal peptide of mouse IgG1 heavy chain (SEQ ID NO: 13) were added to the 5' end of SIRPαD1-coding sequence, and a Kozak sequence (SEQ ID NO: 14) was added to the 5' end of the signal peptide sequence. Lastly, HindIII and NheI restriction sites were added to the 5' and 3' ends of the resulting sequence, respectively. For the light chain, the same signal sequence as well as the Kozac sequence was used, but the HindIII and the XbaI restriction sites were added to the 5' and 3' ends of the resulting sequence, respectively. The two resulting sequences were synthesized by Genscript (ID #: L31834 (heavy chain); M60573 (light chain)) and subcloned, respectively, into the pMac-H and pMac-L vectors.

Example 2. Protein Expression and Purification

To manufacture the recombinant protein IMM2505, the expression vectors were electroporated into Chinese Hamster Ovary (CHO) cells (ATCC, Cat #CCL-61) which were subjected to several rounds of pressure selection of neomycin. The selected stable cells were adapted to a serum-free Balan CD CHO Growth A medium (Irvine Scientific, Cat #94120). For protein expression, cells were seeded in a 3 liter bioreactor and cultured in a fed-batch process. When the cell viability dropped to ~80%, reaction in the bioreactor was terminated, the cell culture supernatant was harvested and subjected to protein purification by affinity chromatography. The purity of recombinant protein was above 95%, and the content of endotoxin was below 0.5 U/g.

Example 3. IMM2505 Bound to PD-L1 or CD47

CHO-PD-L1 cells (over expressing PD-L1) or Jurkat cells (highly expressing CD47) were incubated at 4° C. for 1 hour with serially diluted IMM2505 or control agents. Cells were washed with cold PBS two times, and then incubated with FITC-conjugated secondary antibody against human IgG-Fc (Sigma, Cat #F9512) for 45 min. Cells were washed two times and re-suspended in 200 ml of PBS. Then, the cells were subject to FACS analysis using a flow cytometer (Merck Millipore, Guava® easyCyte 5HT).

Figure 7:
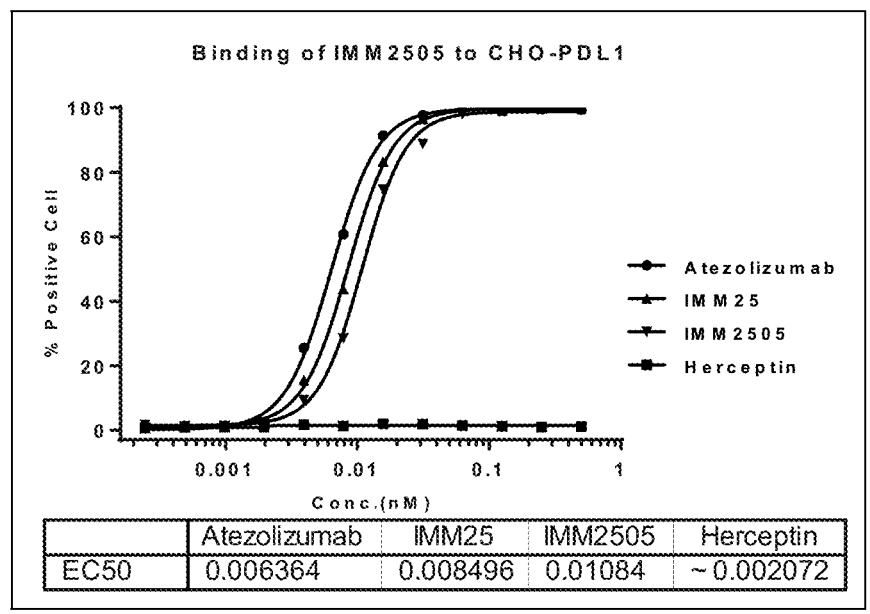
FIG. 7 shows the binding activity of IMM2505 to PD-L1 on CHO cells.
Figure 8:
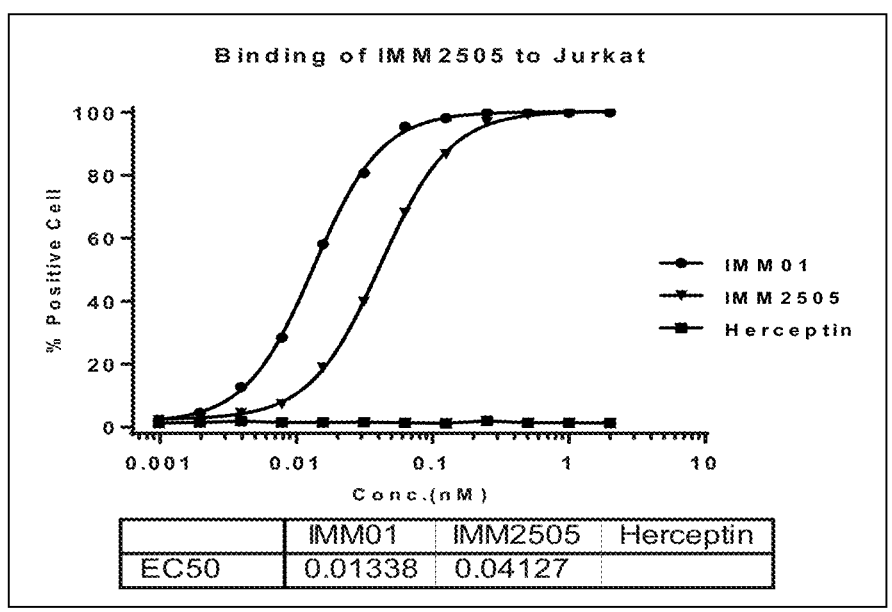
FIG. 8 shows the binding activity of IMM2505 to CD47 on Jurkat cells.

IMM2505 bound to PD-L1 on CHO cells with an $EC_{50}$ value of 0.01 nM (FIG. 7), and bound to CD47 on Jurkat cells with an $EC_{50}$ value of 0.04 nM (FIG. 8), a bit inferior to the traditional single antigen targeting antibodies.

Example 4. IMM2505 Blocked Interaction of PD-L1 with PD-1

Biotin-PD1-Fc was mixed with serially diluted IMM2505, IMM25, Atezoliumab or Herceptin® (trastuzumab), and the mixture was then added to a 96-well plate containing CHO-PD-L1 cells. Cells were incubated at 4° C. for 45 minutes, washed with PBS, and then further incubated at 4° C. for another 45 minutes with PE-conjugated mouse Anti-human CD279 (BD BioScience, Cat #557946). Cells were washed and re-suspended in 200 ml of PBS, and then subjected to FACS analysis for the binding affinity of PD1-Fc with membrane bound PD-L1.

Figure 9:
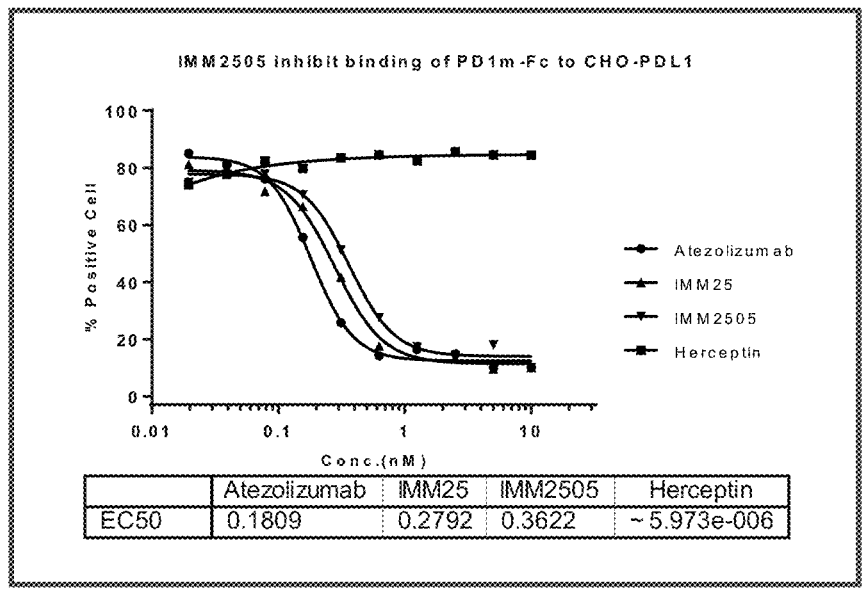
FIG. 9 shows the blockade of PD-L1 on CHO cells by IMM2505.

As shown in FIG. 9, IMM2505 blocked interaction of PD1-Fc with PD-L1+ cells with an $IC_{50}$ value of 0.36 nM.

Example 5. IMM2505 Blocked Interaction of CD47 with SIRPα

FITC-conjugated SIRPa-Fc was mixed with serially diluted IMM2505, IMM01, SIRPα-Fe or Herceptin® (trastuzumab), and the mix was added to a 96-well plate containing Jurkat cells which were incubated at 4° C. for 45 minutes. Cells were washed with PBS and then subjected to FACS analysis for the binding affinity of SIRPα-Fc with membrane bound CD47.

Figure 10:
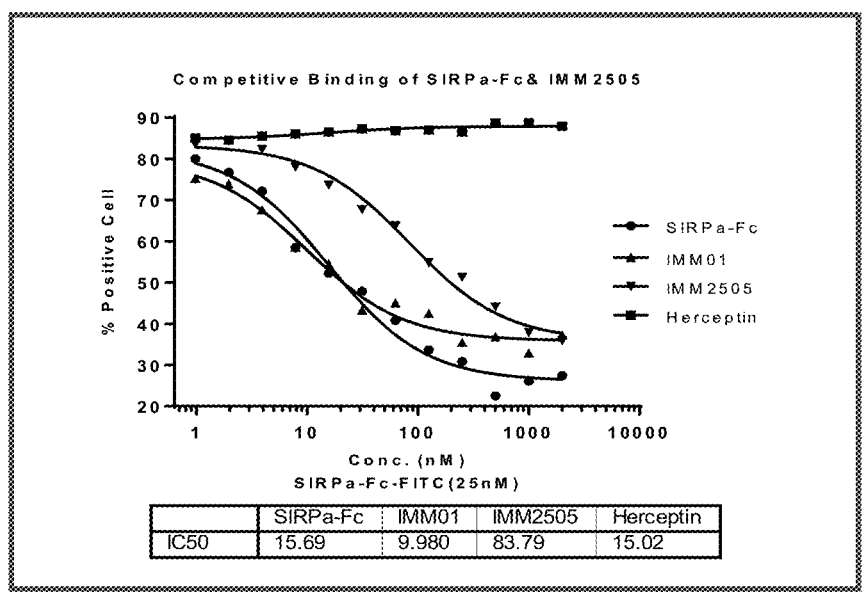
FIG. 10 shows the blockade of CD47 on Jurkat cells by IMM2505.

As shown in FIG. 10, IMM2505 blocked interaction of SIRPα-Fc with CD47+ cells with an $IC_{50}$ value of 83.8 nM.

Example 6. IMM2505 had High Antibody-Dependent Cell-Mediated Cytotoxicity (ADCC)

CFSE-labeled Raji-PD-L1 cells (used as target cells) were mixed with NK92MI cells (effector cells) stably expressing FcγRIIIa at a 1:2 ratio, and the mixed cells were cultured for 4 hours at 37° C. under 5% $CO_2$ in the presence of serially diluted IMM2505 or IMM25. Then propidium iodide (PI) (Sigma, Cat #P4170) was added to the cell culture at a concentration of 5 μg/ml, and the cell culture was subjected to FACS analysis for PI signals. Percentage of cell lysis caused by ADCC was calculated based on the following formula:

% Lysis=(% PI Positive Cell with *IMM*2505 or *IMM*25-% PI Positive Cell with negative control protein)/(100-% PI Positive Cell with negative control protein)*100

Figure 11:
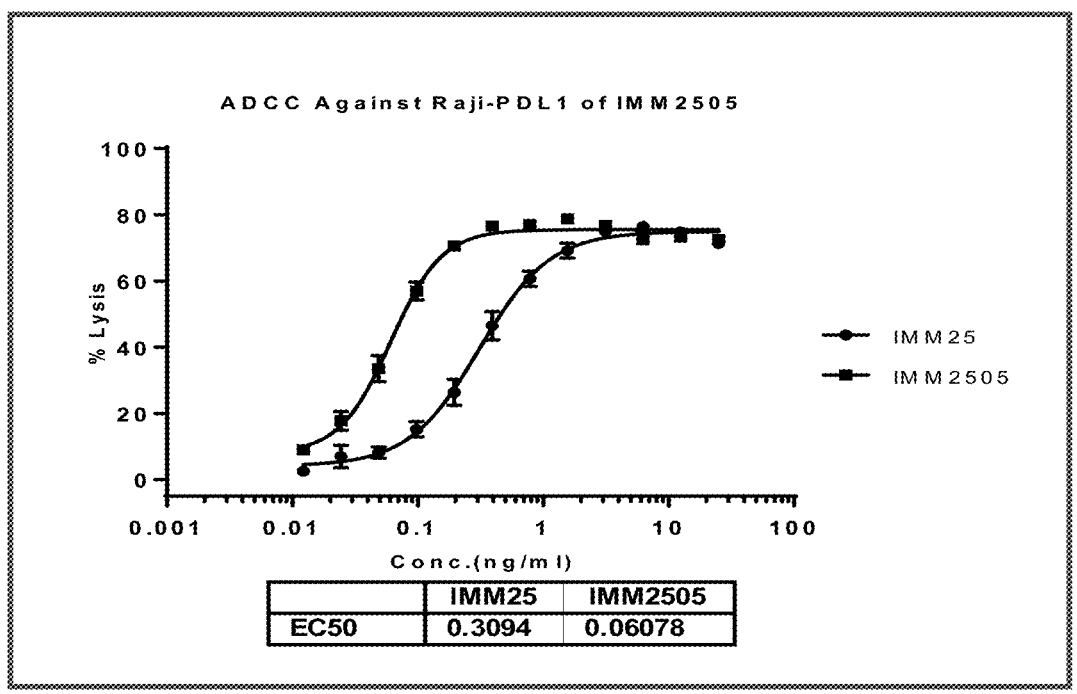
FIG. 11 shows results of ADCC analysis of IMM2505.

As shown in FIG. 11, IMM2505 had a high ADCC activity, almost 5 times that of IMM25.

Example 7. IMM2505 Inhibited Apoptosis of Jurkat-CRP

E1. Development of Chimeric PD-1 Receptor (CPR) Expressing Cell Line

The chimeric PD-1 receptor (CPR) consisted of the extracellular domain of human PD-1, the human CD8a hinge region, the transmembrane and intracellular region of human CD28, and the human CD3ζ. The CPR coding sequence (SEQ ID NO:15) was designed by linking the extracellular domain coding sequence of human PD-1 to that of human CD8a hinge region followed sequentially by the transmembrane and intracellular region of human CD28, and CD3ζ sequence. The resulting sequence was synthesized by Convenience Biology (ID #: T1509090661-T3970) and subcloned into the pMac-Fc vector.

To develop the CPR-expressing cell line, Jurkat cells was electroporated with the expressing vector, and the cells were subjected to several rounds of pressure selection by neomycin. The selected stable cells were confirmed to stably express CPR by FACS analysis using PE Mouse Anti-human CD279 (BD BioScience, Cat #557946).

E2. Induction of Apoptosis of Cell Expressing CPRs

Jurkat-CPR cells at a 96-well plate were mixed with Raji-PD-L1 cells at a ratio of 10:1, and the mixed cells were cultured for 24 hours at 37° C. under 5% $CO_2$. Then, 20 μl of CCK8 (Dojindo, Cat #CK04) was added to the cell solution, and incubated at the cell culture incubator for 2 hours before measuring the optical density (OD) at the wavelength of 450 nm.

E3. Inhibition of PD-L1 Induced Cell Apoptosis

Raji-PD-L1 cells at a 96-well plate were incubated with serially diluted IMM2505, IMM25, Atezoliumab or Herceptin® (trastuzumab) for 45 minutes at 37° C. under 5% $CO_2$, and then the Jurkat-CPR cells were added to the plate, the ratio of Jurkat-CPR cells to Raji-PDL1 cells being 10:1, which was incubated for 24 hours. CCK8 was added to the plate, and the plate was further incubated for another 2 hours before OD measurement at the wavelength of 450 nm.

Figure 12:
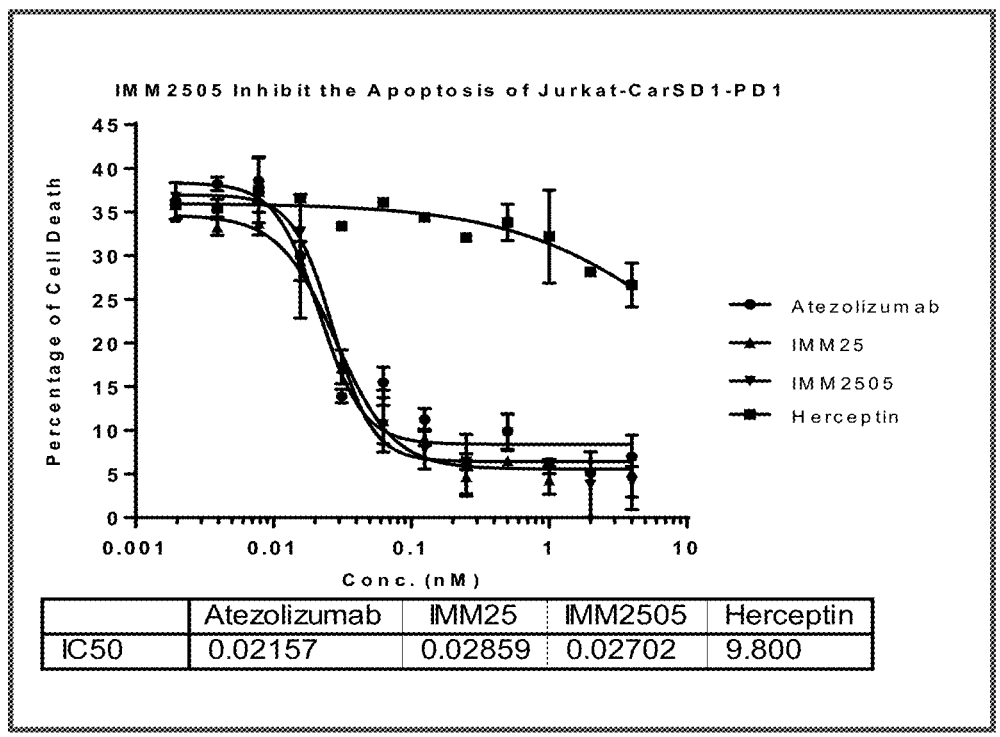
FIG. 12 shows apoptosis inhibition of Jurkat-CPR by IMM2505.

It can be seen from FIG. 12 that IMM2505 inhibited apoptosis of Jurkat-CRP with an $IC_{50}$ value of 0.027 nM.

Example 8. IMM2505 Activated Phagocytosis of HL-60

Mouse macrophage cell line Ana-1 was seeded in a 96-well cell culture plate, $1\times10^5$ cells per well, and cultured for 16-18 hours at 37° C. and 5% $CO_2$. Target cells (HL-60) were labeled with CFSE, and then incubated with serially diluted IMM2505, IMM01 or Herceptin® (trastuzumab) for 45 minutes. The target cell solutions were transferred to the plate containing Ana-1 cells, the ratio of Ana-1 cells to HL-60 cells being 1:1. The mixture was cultured for 2 hours at the cell culture incubator and then subject to analysis by FACS for the density of CFSE in Ana-1 cells.

Figure 13:
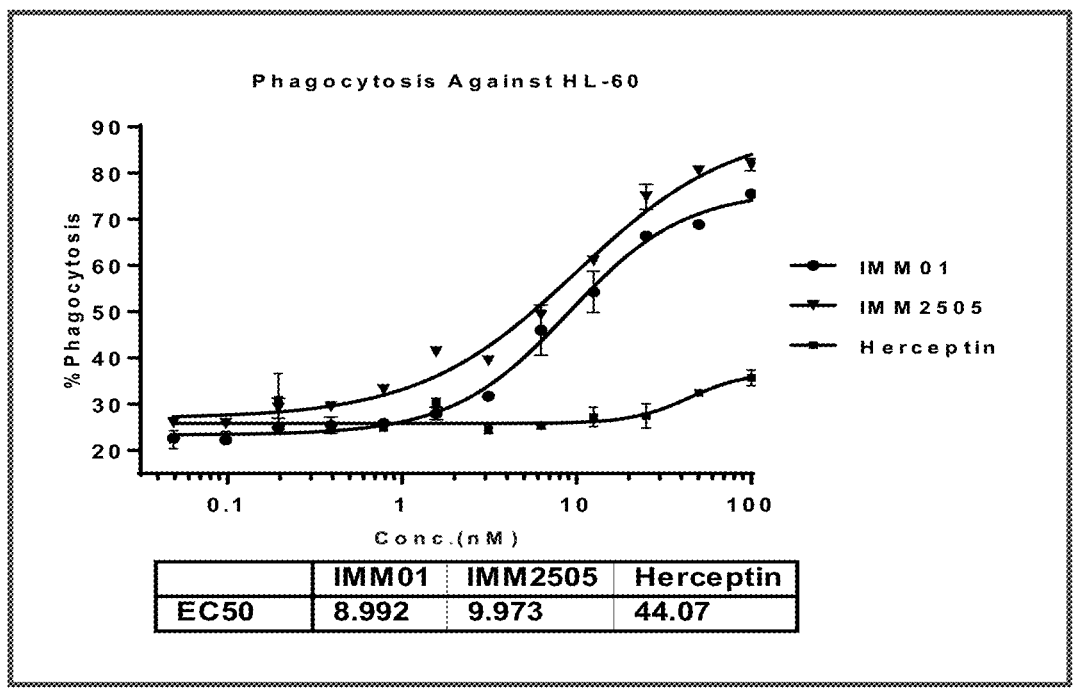
FIG. 13 shows results of ADPC analysis of IMM2505.

FIG. 13 showed that IMM2505 can activate a high level of phagocytosis of tumor cells.

Example 9. IMM2505 had Good Anti-Tumor Effect

Forty-eight 4-6 week old SCID mice were injected subcutaneously with Raji cells, $6\times10^6$ cells per mouse, at the right flank. When tumor volume reached 100-150 $mm^3$, mice were randomly allocated into six groups with 8 mice in each group. Mice were respectively given intraperitoneal injection of PBS, Rituximab-ADCC+ (ADCC-enhancing rituximab, 2.5 mg/kg), IMM2505 (6 mg/kg), IMM25 (5 mg/kg), IMM01 (0.5 mg/kg), and IMM01 plus IMM25 (0.5 mg/kg+5 mg/kg) for 4 weeks, once per week. Tumor volume and body weight were measured every 3-4 days. When the average tumor volume in the PBS group reached 1500 $mm^3$, administrations were stopped and the experiment was terminated.

The tumor volume (V) was calculated as (length×width$^2$)/2. Tumor growth inhibition rate (TGI) was calculated by the formula: Tumor growth inhibition rate=(1-rumor volume change in administration group/tumor volume change in control group)×100%.

TABLE 1

Anti-tumor effect of IMM2505 and other agents

| Group | Drug | Animal # | Dose (mg/kg) | Treatment | TGI | P value |
|---|---|---|---|---|---|---|
| 1 | PBS | 8 | N/A | i.p, q.w. ×4 | | |
| 2 | RTC-ADCC | 8 | 2.5 | i.p, q.w. ×4 | 78.18% | 0.002 |
| 3 | IMM01 | 8 | 0.5 | i.p, q.w. ×4 | 88.24% | 0.0001 |
| 4 | IMM25 | 8 | 5.0 | i.p, q.w. ×4 | 74.84% | 0.002 |
| 5 | IMM2505 | 8 | 6.0 | i.p, q.w. ×4 | 100.06% | 0.0001 |
| 6 | IMM01 + IMM25 | 8 | 0.5 + 5.0 | i.p, q.w. ×4 | 76.44% | 0.002 |

Figure 14:
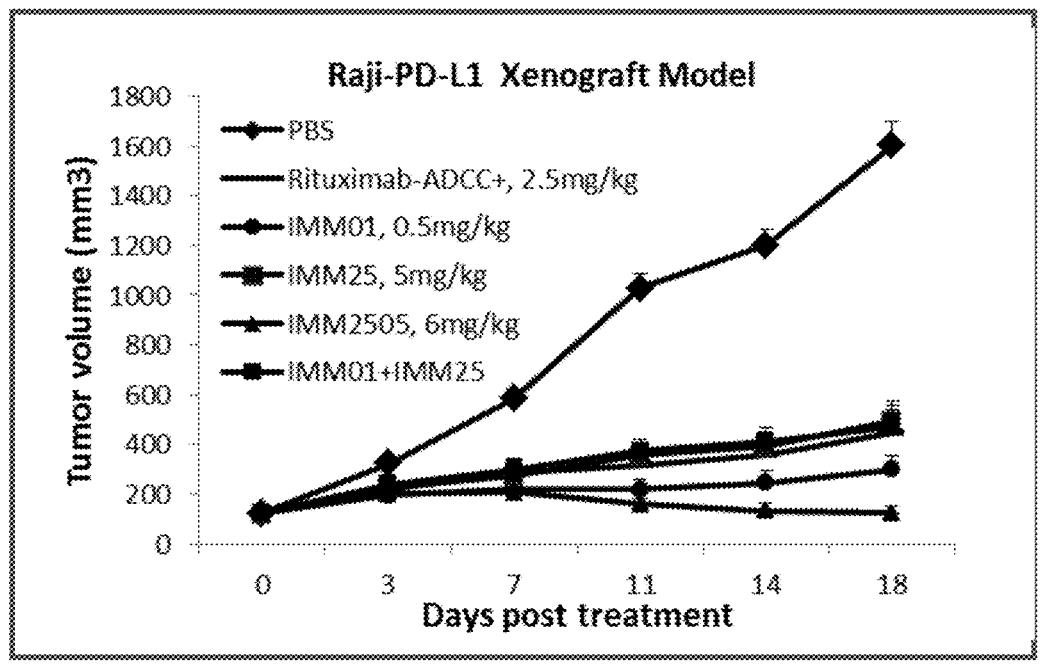
FIG. 14 shows *in vivo* therapeutic efficacy of IMM2505 in Raji-PD-L1 xenograft model.

Group 5 had a tumor growth inhibition rate of 100.06%, which was much higher than those of other groups, as shown in Table 1 above and FIG. 14, suggesting IMM2505's better efficacy compared to the single antigen targeting agents.

While the invention has been described above in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

REFERENCES

1. Fife B T, Pauken K E. The role of the PD-1 pathway in autoimmunity and peripheral tolerance. Annals of the New York Academy of Sciences. 2011, 1217: 45-59
2. Francisco L M, Sage P T, Sharpe A H. The PD-1 pathway in tolerance and autoimmunity. Immunological Reviews. 2010, 236: 219-42
3. Gardai S J, McPhillips K A, Frasch S C, Janssen W J, Starefeldt A, Murphy-Ullrich J E, Bratton D L, Oldenborg P A, Michalak M, Henson P M. Cell-surface calreticulin initiates clearance of viable or apoptotic cells through trans-activation of LRP on the phagocyte. Cell. 2005; 123:321-334
4. Gennaro, ed., Remington: The Science and Practice of Pharmacy, 20th Ed., Lippincott Williams & Wilkins 2003
5. J. R. Robinson, ed., Sustained and Controlled Release Drug Delivery Systems, Marcel Dekker, Inc., New York, 1978
6. Lee W Y, Weber D A, Laur O, Severson E A, McCall I, Jen R P, Chin A C, Wu T, Gernert K M, Parkos C A. Novel Structural Determinants on SIRPa that Mediate Binding to CD47. J Immunol. 2007, 179:7741-7750
7. Obeid M, Panaretakis T, Joza N, Tufi R, Tesniere A, van Endert P, Zitvogel L, Kroemer G. Calreticulin exposure is required for the immunogenicity of gamma-irradiation and UVC light induced apoptosis. Cell Death Differ. 2007, 14:1848-1850
8. Orr A W, Pedraza C E, Pallero M A, Elzie C A, Goicoechea S, Strickland D K, Murphy-Ullrich J E. Low density lipoprotein receptor-related protein is a calreticulin coreceptor that signals focal adhesion disassembly. J Cell Biol. 2003, 161:1179-1189
9. Shields R L, Namenuk A K, Hong K, Meng Y G, Rae J, Briggs J, Xie D, Lai J, Stadlen A, Li B, Fox J A, Presta L G. High Resolution Mapping of the Binding Site on Human IgG1 for FcγRI, FcγRII, FcγRIII, and FcRn and Design of IgG1 Variants with Improved Binding to the FcgR. JBC. 2001, 276:6591-6604
10. Suzanne L. Topalian, F. Stephen Hodi, Julie R. Brahmer, Scott N. Gettinger, David C. Smith, David F. McDermott, John D. Powderly, Richard D. Carvajal, Jeffrey A. Sosman, Michael B. Atkins, Philip D. Leming, David R. Spigel, Scott J. Antonia, Leora Horn, Charles G. Drake, Drew M. Pardoll, Lieping Chen, William H Sharfman, Robert A. Anders, Janis M. Taube, Tracee L. McMiller, Haiying Xu, Alan J. Korman, Maria Jure-Kunkel, Shruti Agrawal, Daniel McDonald, Georgia D. Kollia, Ashok Gupta, Jon M. Wigginton, and Mario Sznol. Safety, Activity, and Immune Correlates of Anti-PD-1 Antibody in Cancer, N Engl J Med 2012; 366:2443-2454
11. Theocharides, A. P. A.; Jin, L. Q.; Cheng, P. Y.; Prasolava, T. K.; Malko, A. V.; Ho, J. M.; Poeppl, A. G.; Rooijen, N. van; Minden, M. D.; Danska, J. S.; Dick, J.; Wang, J. C. Y. J. Exp. Med. 2012, Vol. 209 No. 10 1883-1899
12. Thompson R H, Gillett M D, Cheville J C, Lohse C M, Dong H, Webster W S, Krejci K G, Lobo J R, Sengupta S, Chen L, Zincke H, Blute M L, Strome S E, Leibovich B C, Kwon E D. Costimulatory B7-H1 in renal cell carcinoma patients: Indicator of tumor aggressiveness and potential therapeutic target. PNAS. 2004, 101 (49): 17174-9
13. Tseng D, Volkmer J P, Willingham S B, Contreras-Trujillo H, Fathman J W, Fernhoff N B, Seita J, Inlay M A, Weiskopf K, Miyanishi M, Weissman I L. Anti-CD47 antibody-mediated phagocytosis of cancer by macrophages primes an effective antitumor T-cell response. PNAS. 2013, 110:11103-11108
14. Vlahopoulos, S A. Aberrant control of NF-κB in cancer permits transcriptional and phenotypic plasticity, to curtail dependence on host tissue: molecular mode. Cancer biology & medicine. 2017, 14: 254-270

We claim:

1. A recombinant fusion protein, comprising an anti-PD-L1 antibody and two signal-regulator proteins (SIRP),
   wherein the anti-PD-L1 antibody comprises two heavy chains, two light chains, and a fragment crystallizable region (Fc region),
   wherein each heavy chain has an amino acid sequence of SEQ ID NO: 6,
   wherein each light chain has an amino acid sequence of SEQ ID NO: 8,
   wherein each SIRP comprises an extracellular Ig-like domain,
   wherein each SIRP is SIRPα,
   wherein the extracellular Ig-like domain of SIRPα is SIRPαD1 having an amino acid sequence of SEQ ID NO: 2,
   wherein at least one paratope of the anti-PD-L1 antibody is linked via a linker to SIRPαD1 at an N-terminus of the heavy chain,
   wherein the linker is -(Gly-Gly-Gly-Gly-Ser)$_3$- (SEQ ID NO: 4); and
   wherein the recombinant fusion protein simultaneously binds to CD47 via the SIRP, PD-L1 via at least one paratope of the anti-PD-L1 antibody, and FcR via the Fc region of the anti-PD-L1 antibody.

2. The recombinant fusion protein of claim 1, wherein one paratope of the anti-PDL1 antibody is linked to SIRPαD1 at the N-terminus of the heavy chain.

3. The recombinant fusion protein of claim 1, wherein two paratopes of the anti-PD-L1 antibody are linked to SIRPαD1 at the N-terminus of the heavy chain.

4. A pharmaceutical composition, comprising the recombinant fusion protein of claim 1, and at least one pharmaceutically acceptable excipient.

5. The pharmaceutical composition of claim 4, further comprising at least one pharmaceutically acceptable adjuvant.

6. A method for treating a cancer caused by over-expression of CD47 and/or PD-L1, comprising administering to a patient in need thereof a therapeutically effective amount of the pharmaceutical composition of claim 4.

7. The method of claim 6, wherein the cancer is selected from the group consisting of acute myelocytic leukemia (AML), chronic myelocytic leukemia (CML), acute lymphoblastic leukemia (ALL), non-Hodgkin's lymphoma (NHL), multiple myeloma (MM), bladder cancer, prostate cancer, lung cancer, colon cancer, breast cancer, pancreatic cancer, and renal cell carcinoma.

8. The method of claim 7, wherein the cancer is non-Hodgkin's lymphoma.

\* \* \* \* \*

SEQUENCE LISTING

```
<160> NUMBER OF SEQ ID NOS: 15

<210> SEQ ID NO 1
<211> LENGTH: 375
<212> TYPE: DNA
<213> ORGANISM: Artificial sequence
<220> FEATURE:
<223> OTHER INFORMATION: First extracellular Ig-like domain of SIRPalpha

<400> SEQUENCE: 1
gaggaggagc tgcaggtgat tcagcctgac aagtccgtat cagttgcagc tggagagtcg      60
gccattctgc actgcactgt gacctccctg atccctgtgg ggcccatcca gtggttcaga     120
ggagctggac cagcccggga attaatctac aatcaaaaag aaggccactt cccccgggta     180
acaactgttt cagagtccac aaagagagaa acatggact tttccatcag catcagtgcc      240
atcaccccag cagatgccgg cacctactac tgtgtgaagt tccggaaagg gagccctgac     300
acggagttta agtctggagc aggcactgag ctgtctgtgc gtgccaaacc ctctgccccc     360
```

```
gtggtatcgg gccct                                                      375
```

<210> SEQ ID NO 2
<211> LENGTH: 125
<212> TYPE: PRT
<213> ORGANISM: Artificial sequence
<220> FEATURE:
<223> OTHER INFORMATION: First extracellular Ig-like domain of SIRPalpha

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro
        115                 120                 125

<210> SEQ ID NO 3
<211> LENGTH: 45
<212> TYPE: DNA
<213> ORGANISM: Artificial sequence
<220> FEATURE:
<223> OTHER INFORMATION: Linker

<400> SEQUENCE: 3

```
ggcggcggtg ggagcggcgg cggtgggagc ggcggcgggg gctcg              45
```

<210> SEQ ID NO 4
<211> LENGTH: 15
<212> TYPE: PRT
<213> ORGANISM: Artificial sequence
<220> FEATURE:
<223> OTHER INFORMATION: Linker

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 1347
<212> TYPE: DNA
<213> ORGANISM: Artificial sequence
<220> FEATURE:
<223> OTHER INFORMATION: Heavy chain of anti-PD-L1 antibody

<400> SEQUENCE: 5

```
gaggtgcagc tggtcgagtc tggcggcggc ctcgttcaac caggcgggag cctgcggctc     60
agctgcgccg catctggatt caccttttct gattcttgga tccactgggt tcgccaggcc    120
cctggaaagg gactggagtg ggttgcctgg atctccccat atggtggctc gacttattat    180
gccgactctg tgaaggacag gtttactatc tccgcggaca ctagcaaaaa taccgcatac    240
```

-continued

```
ctgcagatga actctctccg cgctgaagat acagctgtgt actactgcgc aagacgtcac    300
tggcccggcg gattcgacta ttgggggcag ggcactctgg tcaccgtgtc ctccgctagc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc    600
tgcaacgtga atcacaagcc cagcaacacc aaggtggaca agagagttga gcccaaatct    660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtatgtg    840
gacggcgtgg aggtgcataa tgccaagaca aagccgcggg aggagcagta caacgccacg    900
taccgtgtgg tcagcgtcct caccgtcctg caccaagact ggctgaatgg caaggagtac    960
aagtgcaagg tctccaacaa agccctccca gcccccatcg ccgcaaccat ctccaaagcc    1020
aaagggcagc cccgagaacc acaggtgtac accctgcccc catcccggga ggagatgacc    1080
aagaaccaag tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctattccaag ctcaccgtgg acaagagcag gtggcagcag    1260
gggaacgtct tctcatgctc cgtgatgcat gaggctctgc acaaccacta cacgcagaag    1320
agcctctccc tgtctccggg caaatga                                        1347
```

<210> SEQ ID NO 6
<211> LENGTH: 448
<212> TYPE: PRT
<213> ORGANISM: Artificial sequence
<220> FEATURE:
<223> OTHER INFORMATION: Heavy chain of anti-PD-L1 antibody

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
                165                 170                 175
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ala Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Ala Ala Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
435                 440                 445

<210> SEQ ID NO 7
<211> LENGTH: 645
<212> TYPE: DNA
<213> ORGANISM: Artificial sequence
<220> FEATURE:
<223> OTHER INFORMATION: Light chain of anti-PD-L1 antibody

<400> SEQUENCE: 7
gatattcaaa tgacacaaag cccttcttcc ctgagcgctt ctgtgggcga ccgcgttaca      60
atcacatgca gggcaagcca ggatgtcagc actgctgtcg cttggtacca gcagaaacca     120
ggcaaggcac ctaagctcct gatctactcc gcctccttcc tgtattccgg agtcccctcc     180
cgcttttccg gctccgggtc tgggaccgat tcaccctga ccatcagctc cctccagcct      240
gaagattttg ccacctatta ttgtcagcag tacctctatc acccagcgac ctttgggcag     300
gggacaaaag tggagatcaa gcgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
```

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 8
<211> LENGTH: 214
<212> TYPE: PRT
<213> ORGANISM: Artificial sequence
<220> FEATURE:
<223> OTHER INFORMATION: Light chain of anti-PD-L1 antibody

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 9
<211> LENGTH: 1767
<212> TYPE: DNA
<213> ORGANISM: Artificial sequence
<220> FEATURE:
<223> OTHER INFORMATION: SIRP alpha D1-Linker-Anti-PD-L1 heavy chain

<400> SEQUENCE: 9

```
gaggaggagc tgcaggtgat tcagcctgac aagtccgtat cagttgcagc tggagagtcg    60
gccattctgc actgcactgt gacctccctg atccctgtgg ggcccatcca gtggttcaga   120
ggagctggac cagcccggga attaatctac aatcaaaaag aaggccactt ccccgggta   180 acaactgttt cagagtccac aaagagagaa acatggact tttccatcag catcagtgcc    240
atcaccccag cagatgccgg cacctactac tgtgtgaagt tccggaaagg gagccctgac    300
acggagttta gtctggagc aggcactgag ctgtctgtgc gtgccaaacc ctctgccccc    360
```

```
gtggtatcgg gccctggcgg cgtgggagc ggcggcggtg ggagcggcgg cgggggctcg      420
gaggtgcagc tggtcgagtc tggcggcggc ctcgttcaac caggcgggag cctgcggctc      480
agctgcgccg catctggatt cacctttct gattcttgga tccactgggt tcgccaggcc      540
cctggaaagg gactggagtg ggttgcctgg atctccccat atggtggctc gacttattat      600
gccgactctg tgaaggacg gtttactatc tccgcggaca ctagcaaaaa taccgcatac      660
ctgcagatga actctctccg cgctgaagat acagctgtgt actactgcgc aagacgtcac      720
tggcccggcg gattcgacta ttgggggcag ggcactctgg tcaccgtgtc ctccgctagc      780
accaagggcc catcggtctt ccccctggca ccctcctcca agagcacctc tgggggcaca      840
gcggccctgg gctgcctggt caaggactac ttccccgaac cggtgacggt gtcgtggaac      900
tcaggcgccc tgaccagcgg cgtgcacacc ttcccggctg tcctacagtc ctcaggactc      960
tactccctca gcagcgtggt gaccgtgccc tccagcagct gggcaccca gacctacatc     1020 tgcaacgtga atcacaagcc cagcaacacc aaggtggaca gagagttga cccaaatct     1080 tgtgacaaaa ctcacacatg cccaccgtgc ccagcacctg aactcctggg gggaccgtca     1140
gtcttcctct tccccccaaa acccaaggac accctcatga tctcccggac ccctgaggtc     1200
acatgcgtgg tggtggacgt gagccacgaa gaccctgagg tcaagttcaa ctggtatgtg     1260
gacggcgtgg aggtgcataa tgccaagaca aagccgcggg aggagcagta caacgccacg     1320
taccgtgtgg tcagcgtcct caccgtcctg caccagact ggctgaatgg caaggagtac     1380
aagtgcaagg tctccaacaa agccctccca gcccccatcg ccgcaaccat ctccaaagcc     1440
aaagggcagc cccgagaacc acaggtgtac accctgcccc catcccggga ggagatgacc     1500
aagaaccaag tcagcctgac ctgcctggtc aaaggcttct atcccagcga catcgccgtg     1560
gagtgggaga gcaatgggca gccggagaac aactacaaga ccacgcctcc cgtgctggac     1620
tccgacggct ccttcttcct ctattccaag ctcaccgtgg acaagagcag gtggcagcag     1680
gggaacgtct tctcatgctc cgtgatgcat gaggctctgc acaaccacta cacgcagaag     1740
agcctctccc tgtctccggg caaatga                                       1767
```

<210> SEQ ID NO 10
<211> LENGTH: 588
<212> TYPE: PRT
<213> ORGANISM: Artificial sequence
<220> FEATURE:
<223> OTHER INFORMATION: SIRP alpha D1-Linker-Anti-PD-L1 heavy chain

<400> SEQUENCE: 10

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110
```

```
Val Arg Ala Lys Pro Ser Ala Pro Val Val Ser Gly Pro Gly Gly
            115                 120                 125

Gly Ser Gly Gly Gly Ser Gly Gly Gly Ser Glu Val Gln Leu
        130                 135                 140

Val Glu Ser Gly Gly Gly Leu Val Gln Pro Gly Gly Ser Leu Arg Leu
145                 150                 155                 160

Ser Cys Ala Ala Ser Gly Phe Thr Phe Ser Asp Ser Trp Ile His Trp
                165                 170                 175

Val Arg Gln Ala Pro Gly Lys Gly Leu Glu Trp Val Ala Trp Ile Ser
            180                 185                 190

Pro Tyr Gly Gly Ser Thr Tyr Tyr Ala Asp Ser Val Lys Gly Arg Phe
        195                 200                 205

Thr Ile Ser Ala Asp Thr Ser Lys Asn Thr Ala Tyr Leu Gln Met Asn
    210                 215                 220

Ser Leu Arg Ala Glu Asp Thr Ala Val Tyr Tyr Cys Ala Arg Arg His
225                 230                 235                 240

Trp Pro Gly Gly Phe Asp Tyr Trp Gly Gln Gly Thr Leu Val Thr Val
                245                 250                 255

Ser Ser Ala Ser Thr Lys Gly Pro Ser Val Phe Pro Leu Ala Pro Ser
            260                 265                 270

Ser Lys Ser Thr Ser Gly Gly Thr Ala Ala Leu Gly Cys Leu Val Lys
        275                 280                 285

Asp Tyr Phe Pro Glu Pro Val Thr Val Ser Trp Asn Ser Gly Ala Leu
    290                 295                 300

Thr Ser Gly Val His Thr Phe Pro Ala Val Leu Gln Ser Ser Gly Leu
305                 310                 315                 320

Tyr Ser Leu Ser Ser Val Val Thr Val Pro Ser Ser Ser Leu Gly Thr
                325                 330                 335

Gln Thr Tyr Ile Cys Asn Val Asn His Lys Pro Ser Asn Thr Lys Val
            340                 345                 350

Asp Lys Arg Val Glu Pro Lys Ser Cys Asp Lys Thr His Thr Cys Pro
        355                 360                 365

Pro Cys Pro Ala Pro Glu Leu Leu Gly Gly Pro Ser Val Phe Leu Phe
    370                 375                 380

Pro Pro Lys Pro Lys Asp Thr Leu Met Ile Ser Arg Thr Pro Glu Val
385                 390                 395                 400

Thr Cys Val Val Val Asp Val Ser His Glu Asp Pro Glu Val Lys Phe
                405                 410                 415

Asn Trp Tyr Val Asp Gly Val Glu Val His Asn Ala Lys Thr Lys Pro
            420                 425                 430

Arg Glu Glu Gln Tyr Asn Ala Thr Tyr Arg Val Val Ser Val Leu Thr
        435                 440                 445

Val Leu His Gln Asp Trp Leu Asn Gly Lys Glu Tyr Lys Cys Lys Val
    450                 455                 460

Ser Asn Lys Ala Leu Pro Ala Pro Ile Ala Ala Thr Ile Ser Lys Ala
465                 470                 475                 480

Lys Gly Gln Pro Arg Glu Pro Gln Val Tyr Thr Leu Pro Pro Ser Arg
                485                 490                 495

Glu Glu Met Thr Lys Asn Gln Val Ser Leu Thr Cys Leu Val Lys Gly
            500                 505                 510

Phe Tyr Pro Ser Asp Ile Ala Val Glu Trp Glu Ser Asn Gly Gln Pro
        515                 520                 525
```

-continued

Glu Asn Asn Tyr Lys Thr Thr Pro Pro Val Leu Asp Ser Asp Gly Ser
530                 535                 540

Phe Phe Leu Tyr Ser Lys Leu Thr Val Asp Lys Ser Arg Trp Gln Gln
545                 550                 555                 560

Gly Asn Val Phe Ser Cys Ser Val Met His Glu Ala Leu His Asn His
                565                 570                 575

Tyr Thr Gln Lys Ser Leu Ser Leu Ser Pro Gly Lys
                580                 585

<210> SEQ ID NO 11
<211> LENGTH: 1095
<212> TYPE: DNA
<213> ORGANISM: Artificial sequence
<220> FEATURE:
<223> OTHER INFORMATION: SIRP alpha D1-Fc

<400> SEQUENCE: 11
gaggaggagc tgcaggtgat tcagcctgac aagtccgtat cagttgcagc tggagagtcg        60
gccattctgc actgcactgt gacctccctg atccctgtgg ggcccatcca gtggttcaga       120
ggagctggac cagcccggga attaatctac aatcaaaaag aaggccactt cccccgggta       180
acaactgttt cagagtccac aaagagagaa acatggactt ttccatcag catcagtgcc        240
atcaccccag cagatgccgg cacctactac tgtgtgaagt tccggaaagg gagccctgac       300
acggagttta gtctggagc aggcactgag ctgtctgtgc gtgccaaacc ctctgccccc        360
gtggtatcgg ccctgcggc gagggccaca cctcagcacg agcccaaatc ttgtgacaaa       420
actcacacat gcccaccgtg cccagcacct gaactcctgg ggggaccgtc agtcttcctc       480
ttccccccaa aacccaagga caccctcatg atctcccgga cccctgaggt cacatgcgtg       540
gtggtggacg tgagccacga agaccctgag gtcaagttca actggtacgt ggacggcgtg       600
gaggtgcata atgccaagac aaagccgcgg gaggagcagt acaacagcac gtaccgtgtg       660
gtcagcgtcc tcaccgtcct gcaccaggac tggctgaatg gcaaggagta caagtgcaag       720
gtctccaaca agccctccc agcccccatc gagaaaacca tctccaaagc caagggcag        780
ccccgagaac acaggtgta caccctgccc ccatcccggg atgagctgac caagaaccag       840
gtcagcctga cctgcctggt caaaggcttc tatcccagcg acatcgccgt ggagtgggag       900
agcaatgggc agccggagaa caactacaag accacgcctc ccgtgctgga ctccgacggc       960
tccttcttcc tctacagcaa gctcaccgtg gacaagagca ggtggcagca ggggaacgtc      1020
ttctcatgct ccgtgatgca tgaggctctg cacaaccact acacgcagaa gagcctctcc      1080
ctgtctccgg gttga                                                       1095

<210> SEQ ID NO 12
<211> LENGTH: 364
<212> TYPE: PRT
<213> ORGANISM: Artificial sequence
<220> FEATURE:
<223> OTHER INFORMATION: SIRP alpha D1-Fc

<400> SEQUENCE: 12

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Val Ser
 50                  55                  60

Glu Ser Thr Lys Arg Glu Asn Met Asp Phe Ser Ile Ser Ile Ser Ala
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
        115                 120                 125

Ala Thr Pro Gln His Glu Pro Lys Ser Cys Asp Lys Thr His Thr Cys
130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Asp Glu Leu Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly
        355                 360

<210> SEQ ID NO 13
<211> LENGTH: 57
<212> TYPE: DNA
<213> ORGANISM: Artificial sequence
<220> FEATURE:
<223> OTHER INFORMATION: Signal peptide of mouse IgG1 heavy chain

<400> SEQUENCE: 13
atgggatggt catgtatcat ccttttctg gtagcaactg caactggagt acattca        57

<210> SEQ ID NO 14
<211> LENGTH: 9
<212> TYPE: DNA
<213> ORGANISM: Artificial sequence
<220> FEATURE:
<223> OTHER INFORMATION: Kozak

```
<400> SEQUENCE: 14 gccgccacc                                                              9

<210> SEQ ID NO 15
<211> LENGTH: 1107
<212> TYPE: DNA
<213> ORGANISM: Artificial sequence
<220> FEATURE:
<223> OTHER INFORMATION: Chimeric PD-1 receptor coding sequence

<400> SEQUENCE: 15
ttagactccc cagacaggcc ctggaacccc cccaccttct ccccagccct gctcgtggtg      60
accgaagggg acaacgccac cttcacctgc agcttctcca acacatcgga gagcttcgtg     120
ctaaactggt accgcatgag ccccagcaac cagacggaca agctggccgc cttccccgag     180
gaccgcagcc agcccggcca ggactgccgc ttccgtgtca cacaactgcc caacgggcgt     240
gacttccaca tgagcgtggt cagggcccgg cgcaatgaca gcggcaccta cctctgtggg     300
gccatctccc tggccccaa ggcgcagatc aaagagagcc tgcgggcaga gctcagggtg     360
acagagagaa gggcagaagt gcccacagcc cacccagcc cctcacccag gccagccggc     420
cagttccaaa ccacgacgcc agcgccgcga ccaccaacac cggcgcccac catcgcgtcg     480
cagcccctgt ccctgcgccc agaggcgtgc cggccagcgg cggggggcgc agtgcacacg     540 aggggctgg acttcgcctg tgatttttgg gtgctggtgg tggttggtgg agtcctggct     600
tgctatagct tgctagtaac agtggccttt attattttct gggtgaggag taagaggagc     660
aggctcctgc acagtgacta catgaacatg actccccgcc gccccgggcc cacccgcaag     720
cattaccagc cctatgcccc accacgcgac ttcgcagcct atcgctccag agtgaagttc     780
agcaggagcg cagagccccc cgcgtaccag cagggccaga accagctcta taacgagctc     840
aatctaggac gaagagagga gtacgatgtt ttggacaaga gacgtggccg ggaccctgag     900 atgggggaa agccgagaag gaagaaccct caggaaggcc tgtacaatga actgcagaaa     960
gataagatgg cggaggccta cagtgagatt gggatgaaag gcgagcgccg gaggggcaag    1020
gggcacgatg gcctttacca gggtctcagt acagccacca aggacaccta cgacgccctt    1080
cacatgcagg ccctgccccc tcgctaa                                        1107
```